US00PP26362P2

(12) United States Plant Patent
Trees

(10) Patent No.: US PP26,362 P2
(45) Date of Patent: Jan. 26, 2016

(54) ***SALVIA* PLANT NAMED 'RADIO RED'**

(50) Latin Name: *Salvia×hybrida*
Varietal Denomination: Radio Red

(71) Applicant: Ball Horticultural Company, West Chicago, IL (US)

(72) Inventor: Scott Trees, Arroyo Grande, CA (US)

(73) Assignee: Ball Horticultural Company, West Chicago, IL (US)

( * ) Notice: Subject to any disclaimer, the term of this patent is extended or adjusted under 35 U.S.C. 154(b) by 19 days.

(21) Appl. No.: 14/121,128

(22) Filed: Aug. 4, 2014

(51) Int. Cl.
*A01H 5/02* (2006.01)

(52) U.S. Cl.
USPC ..... Plt./475

(58) Field of Classification Search
USPC ..... Plt./475
CPC ..... A01H 5/02; A01H 5/00
See application file for complete search history.

*Primary Examiner* — Kent L Bell
(74) *Attorney, Agent, or Firm* — Audrey Charles

(57) ABSTRACT

A new and distinct cultivar of *Salvia* plant named 'Radio Red', characterized by its bright red-colored flowers, dark green-colored foliage, and moderately vigorous, upright growth habit, is disclosed.

1 Drawing Sheet

Latin name of genus and species of plant claimed: *Salvia× hybrida.*

Variety denomination: 'Radio Red'.

BACKGROUND OF THE INVENTION

The present invention relates to a new and distinct cultivar of *Salvia* plant botanically known as *Salvia×hybrida* and hereinafter referred to by the cultivar name 'Radio Red'.

The new cultivar originated in a controlled breeding program in Buellton, Calif. during the summer of 2008. The objective of the breeding program was the development of *Salvia* cultivars having large flowers and compact growth habits.

The new *Salvia* cultivar is the result of open-pollination. The female (seed) parent of the new cultivar is Mesa Azure, 'Mes Azur', U.S. Plant Pat. No. 21,097 characterized by its medium violet-colored flowers, medium green-colored foliage, and moderately vigorous, upright growth habit. The male (pollen) parent of the new cultivar is unknown. The new cultivar was discovered and selected as a single flowering plant within the progeny of the above stated open-pollination during November 2009 in a controlled environment in Buellton, Calif.

Asexual reproduction of the new cultivar by terminal stem cuttings since November 2009 in Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Radio Red' as a new and distinct cultivar of *Salvia* plant:

1. Bright red-colored flowers;
2. Dark green-colored foliage; and
3. Moderately vigorous, upright growth habit.

Plants of the new cultivar differ from plants of the female parent primarily in flower color.

Of the many commercially available *Salvia* cultivars, the most similar in comparison to the new cultivar is 'Furman's Red', not patented. However, in side by side comparisons, plants of the new cultivar differ from plants of 'Furman's Red' in at least the following characteristics:

1. Plants of the new cultivar are shorter than plants of 'Furman's Red'; and
2. Plants of the new cultivar have larger flowers than plants of 'Furman's Red'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Radio Red'. The plants were grown in one-gallon containers for approximately two months in a greenhouse and one month outdoors in Elburn, Ill. Plants were given one pinch prior to transplant and one pinch two weeks after transplant.

DETAILED BOTANICAL DESCRIPTION

Figure 1:
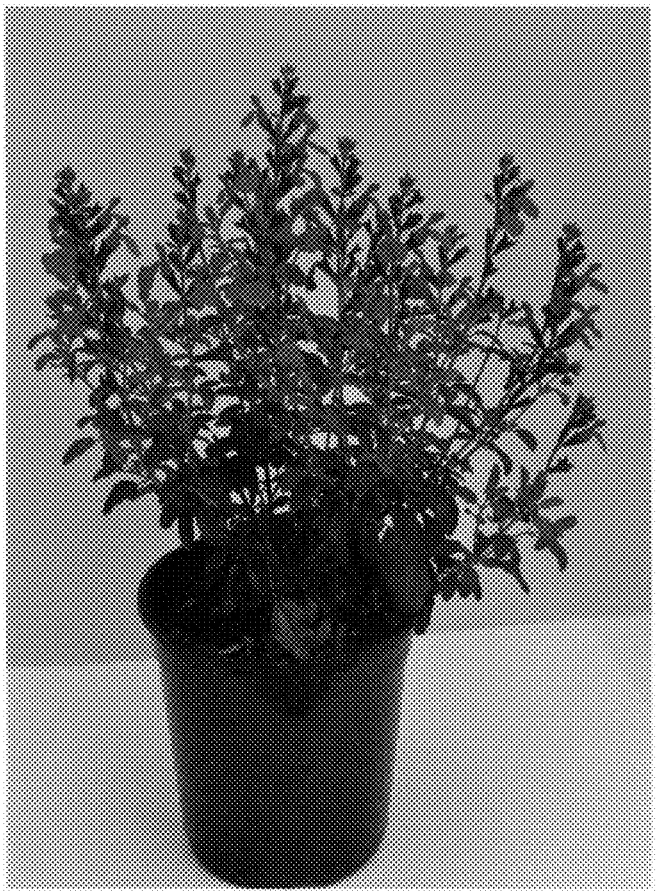
FIG. 1 illustrates a side view of the overall growth and flowering habit of 'Radio Red'.
Figure 2:
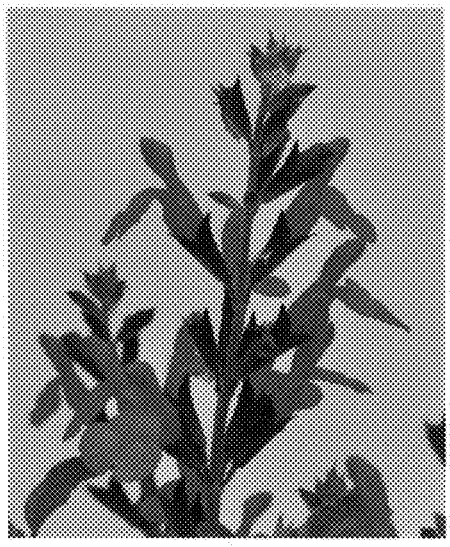
FIG. 2 illustrates a close-up view of an inflorescence of 'Radio Red'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in June 2014 under natural light conditions in West Chicago, Ill.

The following descriptions and measurements describe plants produced from cuttings from stock plants and grown under conditions comparable to those used in commercial practice. The plants were grown utilizing a soilless growth medium in one-gallon containers for approximately two months in a greenhouse and one month outdoors in Elburn, Ill. Plants were given one pinch prior to transplant and one pinch two weeks after transplant. Greenhouse temperatures were maintained at approximately 45° F. to 65° F. (7.2° C. to 18.3° C.) during the day and approximately 35° F. to 45° F. (1.7° C. to 7.2° C.) during the night. No supplemental lighting was provided. Measurements and numerical values represent averages of typical plants.

Botanical classification: *Salvia×hybrida* cultivar Radio Red.

Parentage:

*Female parent.*—Mesa Azure, 'Mes Azur', U.S. Plant Pat. No. 21,097.

*Male parent.*—Unknown.

Propagation:

*Type cutting.*—Terminal stem.

*Time to initiate roots.*—Approximately 12 to 15 days.

*Time to produce a rooted cutting.*—Approximately 35 to 42 days.

*Root description.*—Fine, fibrous white to dark brown in color.

*Rooting habit.*—Freely branching.

Plant description:

*Commercial crop time.*—Approximately 12 to 14 weeks from a rooted cutting to finish in a 15 cm pot.

*Growth habit and general appearance.*—Moderately vigorous, upright growth habit.

*Size.*—Height from soil level to top of plant plane: Approximately 28.8 cm. Width: Approximately 29.5 cm.

*Branching habit.*—Freely branching. Pinching enhances lateral branching. Quantity of branches per plant: Approximately 3 main basal branches and approximately 20 lateral branches.

*Branch.*—Shape: Square in cross section. Strength: Strong. Length to base of inflorescence: Approximately 13.0 cm. Diameter: Approximately 3.0 mm. Length of central internode: Approximately 1.8 cm. Texture: Densely pubescent with appressed, soft, short hairs. Color of young stem: 144A. Color of mature stem: 144A, becoming woody 200C with age.

Foliage description:

*General description.*—Quantity of leaves per branch: Approximately 8. Fragrance: Slight, sage-like. Form: Simple. Arrangement: Opposite.

*Leaves.*—Aspect: Perpendicular angle to stem with tips downward turning. Shape: Elliptic. Margin: Crenate. Apex: Obtuse. Base: Obtuse. Venation pattern: Pinnate. Length of mature leaf: Approximately 3.5 cm. Width of mature leaf: Approximately 1.6 cm. Texture of upper and lower surfaces: Rugous, moderately pubescent. Color of upper surface of young and mature foliage: N137B with venation of 144D. Color of lower surface of young and mature foliage: Closest to 138B with venation of 144D.

*Petiole.*—Length: Approximately 1.1 cm. Diameter: Approximately 1.5 mm. Texture: Densely pubescent. Color: 144D.

Flowering description:

*Flowering habit.*—'Radio Red' is freely flowering under outdoor growing conditions blooming from early spring through late summer and with limited flowering under short winter days in a greenhouse environment.

*Lastingness of individual floret.*—Approximately 4 to 5 days.

Inflorescence description:

*General description.*—Type: Terminal raceme, not persistent. Quantity of inflorescences per plant: Approximately 17. Fragrance: Faint. Length or height of inflorescence: Approximately 11.5 cm. Width of inflorescence: Approximately 5.5 cm. Quantity of fully-open flowers per inflorescence: Approximately 6.

*Peduncle.*—Shape: Square in cross section. Strength: Strong. Aspect: Erect. Length: Approximately 2.5 cm. Diameter: Approximately 2.0 mm. Texture: Densely pubescent with appressed, soft, short hairs. Color: 144A.

Flower description:

*Type.*—Single, zygomorphic.

*Bud.*—Rate of opening: Generally takes 2 to 3 days for bud to progress from first color to fully open flower.

*Bud just before opening.*—Shape: Obovoid. Length: Approximately 1.0 cm. Diameter: Approximately 6.0 mm. Texture: Densely pubescent. Color: Calyx of 144B with venation of N186A; petals of 59A.

*Corolla.*—Shape: Bilabiate, lower lip having three highly-fused lobes. Width: Approximately 1.7 cm. Length: Approximately 1.9 cm. Depth: Approximately 2.9 cm.

*Upper lip.*—Shape: Hooded. Margin: Entire. Apex: Rounded. Length from throat: Approximately 1.1 cm. Width: Approximately 5.0 mm. Texture of inner surface: Glabrous. Texture of outer surface: Densely pubescent. Pubescent color: 59A. Color of inner surface when first and fully open: NN155D with an overlay of N74D at edges. Color of outer surface when first and fully open: 53A to 53B.

*Lower lip.*—Shape of central lobe: Orbicular, cupped. Margin of central lobe: Entire, scalloped. Shape of lateral lobes: Oblong. Margin of lateral lobes: Entire. Apex of central lobe: Emarginate. Apex of lateral lobes: Rounded. Length from throat of central lobe: Approximately 1.5 cm. Width of central lobe: Approximately 1.7 cm. Length from throat of lateral lobes: Approximately 7.0 mm. Width of lateral lobes: Approximately 3.0 mm. Texture of upper surface: Glabrous. Texture of lower surface: Sparsely pubescent. Color of upper surface when first and fully open: 45B. Color of lower surface when first and fully open: 45D.

*Calyx.*—Shape: Tubular. Length: Approximately 1.4 cm. Diameter: Approximately 7.0 mm.

*Sepals.*—Quantity per flower: 3, fused to form a tube. Apex: Acute. Length of free portion: Approximately 5.0 mm. Width of larger sepal: Approximately 7.0 mm. Width of two smaller sepals: Approximately 4.0 mm. Texture of inner surface: Glabrous. Texture of outer surface: Densely pubescent. Color of inner surface: 137C with an overlay of N186A. Color of outer surface: 144B with venation and apex of N186A.

*Pedicel.*—Strength: Strong, flexible. Aspect: At an acute angle. Length: Approximately 5.0 mm. Diameter: Approximately 1.5 mm. Texture: Densely pubescent. Color: 137C, occasionally with an overlay of 187A.

*Reproductive organs.*—Androecium: Stamen quantity: 2 per flower, dorsifixed. Stamen length: Approximately 1.5 cm. Filament length: Approximately 1.3 cm. Filament color: NN155D, opaque with an overlay of N74B. Anther shape: Narrowly elliptic to oblong. Anther length: Approximately 2.0 mm. Anther color: 186C. Pollen amount: Abundant. Pollen color: 9A. Gynoecium: Pistil quantity: 1 per flower. Pistil length: Approximately 2.9 cm. Stigma shape: Cleft, two-parted, strongly curved. Stigma length: Approximately 3.0 mm. Stigma color: N80B. Style length: Approximately 2.4 cm. Style color: NN155D. Ovary length: Approximately 2.0 mm. Ovary color: 144D.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Radio Red', substantially as herein shown and described.

* * * * *